(12) United States Patent
Kamon

(10) Patent No.: US 11,911,007 B2
(45) Date of Patent: Feb. 27, 2024

(54) IMAGE PROCESSING DEVICE, ENDOSCOPE SYSTEM, AND IMAGE PROCESSING METHOD

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 857 days.

(21) Appl. No.: 17/000,374

(22) Filed: Aug. 24, 2020

(65) Prior Publication Data

US 2020/0383553 A1 Dec. 10, 2020

Related U.S. Application Data

(63) Continuation of application No. PCT/JP2019/005058, filed on Feb. 13, 2019.

(30) Foreign Application Priority Data

Mar. 2, 2018 (JP) ................................ 2018-037630

(51) Int. Cl.
  *G06V 10/25* (2022.01)
  *A61B 1/045* (2006.01)
  (Continued)

(52) U.S. Cl.
  CPC ........ *A61B 1/045* (2013.01); *A61B 1/000094* (2022.02); *A61B 1/00117* (2013.01);
  (Continued)

(58) Field of Classification Search
  CPC ....... G06V 10/25; G06V 10/764; G06F 18/24
  See application file for complete search history.

(56) References Cited

U.S. PATENT DOCUMENTS

| 2011/0115882 A1* | 5/2011 | Shahinian .......... A61B 1/00193 348/E13.001 |
| 2012/0013773 A1 | 1/2012 | Yoshino et al. |

(Continued)

FOREIGN PATENT DOCUMENTS

| JP | 2010094153 | 4/2010 |
| JP | 2013165776 | 8/2013 |

(Continued)

OTHER PUBLICATIONS

"International Search Report (Form PCT/ISA/210) of PCT/JP2019/005058," dated May 7, 2019, with English translation thereof, pp. 1-5.

(Continued)

Primary Examiner — Myron Wyche
(74) Attorney, Agent, or Firm — JCIPRNET

(57) ABSTRACT

An object of the present invention is to provide an image processing device, an endoscope system, and an image processing method capable of observing an accurate structure of a subject while preventing a substantial decrease in a frame rate in a case where an image is acquired using a plurality of observation lights. An image processing device according to a first aspect of the present invention includes an image input unit that inputs a first image and a second image captured at different times, in which the image input unit inputs the first image captured with first observation light and the second image captured with second observation light different from the first observation light; a parameter calculation unit that calculates a parameter for registering the first image and the second image; an image generation unit that applies the parameter to the first image to generate a registered first image; and a display control unit that causes a display device to sequentially display the input first image and the generated registered first image.

20 Claims, 11 Drawing Sheets

(51) Int. Cl.
*A61B 1/00* (2006.01)
*G06F 18/24* (2023.01)
*G06V 10/141* (2022.01)
*G06V 10/75* (2022.01)
*G06V 10/764* (2022.01)
*G06V 10/143* (2022.01)

(52) U.S. Cl.
CPC .......... *A61B 1/00126* (2013.01); *G06F 18/24* (2023.01); *G06V 10/141* (2022.01); *G06V 10/143* (2022.01); *G06V 10/25* (2022.01); *G06V 10/754* (2022.01); *G06V 10/764* (2022.01)

(56) References Cited

U.S. PATENT DOCUMENTS

| | | | | |
|---|---|---|---|---|
| 2012/0194873 | A1* | 8/2012 | Fu | H04N 1/047 358/448 |
| 2013/0158352 | A1* | 6/2013 | Imaizumi | A61B 1/0638 600/111 |
| 2013/0211217 | A1 | 8/2013 | Yamaguchi et al. | |
| 2013/0293682 | A1* | 11/2013 | Zouda | H04N 13/221 348/46 |
| 2015/0187057 | A1* | 7/2015 | Kobayashi | H04N 9/3185 345/647 |
| 2015/0265142 | A1* | 9/2015 | Ogawa | G02B 23/2476 600/109 |
| 2017/0014059 | A1 | 1/2017 | Koshiba | |
| 2017/0042413 | A1* | 2/2017 | Igarashi | A61B 1/045 |
| 2018/0249889 | A1 | 9/2018 | Imai | |
| 2018/0263712 | A1* | 9/2018 | Kitamura | A61B 34/20 |
| 2018/0333045 | A1* | 11/2018 | Yamanashi | A61B 1/000094 |

FOREIGN PATENT DOCUMENTS

| | | |
|---|---|---|
| JP | 2013202189 | 10/2013 |
| JP | 2015223249 | 12/2015 |
| WO | 2010109950 | 9/2010 |
| WO | 2015151929 | 10/2015 |
| WO | 2017110180 | 6/2017 |

OTHER PUBLICATIONS

"Written Opinion of the International Searching Authority (Form PCT/ISA/237) of PCT/JP2019/005058," dated May 7, 2019, with English translation thereof, pp. 1-7.

Office Action of Japan Counterpart Application, with English translation thereof, dated Feb. 15, 2021, pp. 1-4.

* cited by examiner

IMAGE PROCESSING DEVICE, ENDOSCOPE SYSTEM, AND IMAGE PROCESSING METHOD

CROSS-REFERENCE TO RELATED APPLICATIONS

The present application is a Continuation of PCT International Application No. PCT/JP2019/005058 filed on Feb. 13, 2019 claiming priority under 35 U.S.C § 119(a) to Japanese Patent Application No. 2018-037630 filed on Mar. 2, 2018. Each of the above applications is hereby expressly incorporated by reference, in its entirety, into the present application.

BACKGROUND OF THE INVENTION

1. Field of the Invention

The present invention relates to an image processing device, an endoscope system, and an image processing method, and particularly to the image processing device, the endoscope system, and the image processing method for acquiring an image with a plurality of observation lights.

2. Description of the Related Art

In a medical field, an image of a subject captured using medical appliances is used for diagnosis, treatment, or the like, but "what kind of structure of the subject is clearly (or unclearly) reflected in the captured image" depends on observation light used for imaging. For example, in an image captured under special light such as narrow-band light having a strong short-wavelength component, blood vessels in the surface layer are depicted with high contrast, which is suitable for lesion detection. On the other hand, in an image captured under special light having a strong long-wavelength component, blood vessels in the deep layer are depicted with high contrast. In addition, the observation by a doctor is often performed using normal light (white light) instead of special light. As described above, in imaging, it is preferable to perform irradiation of observation light according to the purpose of use of an image, and in a case where an image is used for a plurality of purposes, it is necessary to perform irradiation of different observation lights to capture an image. Further, depending on the purpose of use of an image, there is a case where it is desired to continuously acquire the image without decreasing a frame rate (for example, in a case of observing).

As a technique for capturing a plurality of images corresponding to different observation lights, for example, the technique described in the following documents is known. JP2015-223249A discloses a processor for an endoscope that displays a narrow-band image in which a specific part of a subject is emphasized and a color pseudo image in which a color image of the subject obtained by white light is expressed in a pseudo manner in a single screen. In addition, JP2010-094153A discloses an electronic endoscope system that simultaneously acquires a normal light image (an image obtained through irradiation of white light) and a special light image (an image obtained through irradiation of special light having a narrow wavelength range).

SUMMARY OF THE INVENTION

In the technique disclosed in JP2015-223249A, the narrow-band image (the image by narrow-band light) is color-converted by a color conversion matrix to generate the color pseudo image (the image obtained through irradiation of the white light). However, as described above, since the structure of the subject reflected in the image varies depending on the wavelength of observation light, it is difficult to accurately consider the structure in image generation by the color conversion. In addition, in the technique described in JP2010-094153A, white light and narrow-band special light are simultaneously irradiated at one time among a plurality of imaging operations while the white light is constantly irradiated. In such a frame of simultaneous irradiation, the wavelength ranges of the white light and the special light are mixed, but it is difficult to separate the wavelength (to remove the influence of the other wavelength).

As described above, in the related art, in a case where an image is acquired using a plurality of observation lights, it is difficult to observe an accurate structure of a subject while preventing a substantial decrease in a frame rate.

The present invention has been made in view of such circumstances, and an object of the present invention is to provide an image processing device, an endoscope system, and an image processing method capable of observing an accurate structure of a subject while preventing a substantial decrease in a frame rate in a case where an image is acquired using a plurality of observation lights.

In order to achieve the above-described object, an image processing device according to a first aspect of the present invention comprises an image input unit that inputs a first image and a second image captured at different times, in which the image input unit inputs the first image captured with first observation light and the second image captured with second observation light different from the first observation light; a parameter calculation unit that calculates a parameter for registering the first image and the second image; an image generation unit that applies the parameter to the first image to generate a registered first image; and a display control unit that causes a display device to sequentially display the input first image and the generated registered first image.

In the first aspect, the first image captured by the first observation light and the second image captured by the second observation light are used. The second observation light is not used to capture the first image, and the first observation light is not used to capture the second image. In addition, since the registered first image is generated and displayed, a substantial loss of frames does not occur in a case where the first image is displayed. Further, since the parameter for registering is applied to the first image to generate the registered first image, it is possible to reduce changes in a tint and a structure of the subject between frames. As described above, according to the first aspect, in a case where an image is acquired using a plurality of observation lights, it is possible to observe an accurate structure of a subject while preventing a substantial decrease in a frame rate. In the first aspect and each of the following aspects, the "registered first image" means "a first image at a capturing time of the second image, which is generated by applying a parameter for registering to the first image".

In the first aspect and each of the following aspects, one of the first observation light and the second observation light may be white light and the other may be narrow-band light, or both may be different narrow-band light. As the first observation light and the second observation light, light emitted from a light source may be used as it is, or light generated by applying a filter that causes the light (for example, white light) emitted from the light source to transmit a specific wavelength range may be used. In addition, in a case where narrow-band light is used as the first observation light and/or the second observation light, the narrow-band light to be used may be narrow-band light irradiated from a light source for narrow-band light or narrow-band light generated by applying a filter that causes white light to transmit a specific wavelength range. In this case, different narrow-band lights may be irradiated at different timings by sequentially switching the filters.

In the first aspect and each of the following aspects, "the first observation light and the second observation light are different" means that at least one of a wavelength range or an optical spectrum is not the same between the first observation light and the second observation light. In addition, the second image can be displayed as necessary (for example, according to an instruction input by a user or according to a result of processing the second image). Further, the first image and the second image may be an image for medical use obtained by capturing a subject such as a living body.

In the first aspect and each of the following aspects, the image for medical use is also referred to as a medical image. As a light source used in a case of capturing the image for medical use, a light source that generates light in a white range, light including a plurality of wavelengths (narrow-band light) in a white range, infrared light, or excitation light can be used. In addition, the image for medical use acquired in the first aspect may be a normal light image obtained through irradiation of light in a white range or light including a plurality of wavelength ranges as light in a white range, or may be a special light image having information of a specific wavelength range acquired on the basis of a normal light image.

The image processing device according to a second aspect is the image processing device according to the first aspect, in which the parameter calculation unit calculates, as the parameter, a parameter for at least one of relative movement, rotation, or deformation between the first image and the second image. The second aspect defines contents of the parameter for registering. The "deformation" can include enlargement and reduction.

The image processing device according to a third aspect is the image processing device according to the first or second aspect, in which the parameter calculation unit calculates, as the parameter, a parameter for performing projective transformation between the first image and the second image, and in which the image generation unit performs projective transformation based on the calculated parameter on the first image to generate the registered first image. The third aspect defines one aspect of registration.

An image processing device according to a fourth aspect is the image processing device according to any one of the first to third aspects, in which the image input unit acquires the first image captured at a capturing time which is before a capturing time of the second image and at which a time difference from the capturing time of the second image is equal to or less than a threshold value. In a case of using the first image captured at a capturing time after the capturing time of the second image, there is a possibility that generation and display of the registered first image are delayed depending on a time difference between the capturing times. In addition, in a case where the time difference between the capturing times exceeds the threshold value, there is a possibility that an imaging range, an imaging angle, and the like change due to the movement of the subject or the like, and registering accuracy decreases. In view of the above circumstances, in the fourth aspect, the image input unit acquires the first image captured at a capturing time which is before a capturing time of the second image and at which a time difference from the capturing time of the second image is equal to or less than a threshold value. As a result, it is possible to generate the registered first image in which a change in the structure of the subject is small compared to the first image.

The image processing device according to a fifth aspect is the image processing device according to any one of the first to fourth aspects, further comprising an image correction unit that performs correction on the first image and/or the second image to reduce a difference between the first image and the second image caused by a difference between the first observation light and the second observation light, in which the parameter calculation unit calculates the parameter for the corrected first image and the corrected second image. As described above, the structure of the subject reflected in the image varies due to the difference of the observation light (wavelength balance), and in the case where the structure of the subject reflected in the image varies, the structure of the object in the registered first image may be changed compared to the first image. In view of the above circumstances, in the fifth aspect, the image correction unit performs correction (pre-processing for registration) that reduces the difference between the first image and the second image. As a result, since the first image and the second image can be accurately registered with each other, it is possible to generate the registered first image in which a change in the structure of the subject is small compared to the first image.

The image processing device according to a sixth aspect is the image processing device according to the fifth aspect, in which the image correction unit extracts a component of a wavelength common to the first observation light and the second observation light from an image signal of the first image and an image signal of the second image, and in which the parameter calculation unit calculates the parameter on the basis of the extracted component. The sixth aspect defines one aspect of the correction in the fifth aspect, and it is possible to calculate a parameter that enables accurate registration.

The image processing device according to a seventh aspect is the image processing device according to the sixth aspect, in which the image correction unit weights at least one of the image signal of the first image or an image signal of the second image to make a signal intensity of a component having a wavelength common to the first observation light and the second observation light relatively stronger than a signal intensity of other components other than the component, and in which the parameter calculation unit calculates the parameter using the weighted image signal. The seventh aspect more specifically defines the parameter calculation in the sixth aspect.

The image processing device according to an eighth aspect is the image processing device according to any one of the first to seventh aspects, further comprising a detection unit that detects a region of interest from the first image, the registered first image, or the second image. According to the eighth aspect, it is possible to detect the region of interest in parallel while sequentially displaying the first image and the registered first image. The region of interest can be detected in any of the first image, the registered first image, or the second image.

The image processing device according to a ninth aspect is the image processing device according to the eighth aspect, further comprising a first output unit that outputs information indicating the region of interest. In the ninth aspect, the output of the information indicating the region of interest can be performed by screen display, audio output, or the like, and thereby the user can easily recognize the information on the region of interest.

The image processing device according to a tenth aspect is the image processing device according to the ninth aspect, in which the display control unit superimposes the information indicating the region of interest on the first image and causes the display device to display the information. In the tenth aspect, the superimposed display of the information can be performed by characters, numbers, figures, symbols, colors, or the like according to a detection result (for example, a position, size, or the like of the region of interest), and thereby the user can easily recognize the information on the region of interest.

The image processing device according to an eleventh aspect is the image processing device according to any one of the eighth to tenth aspects, further comprising a classification unit that classifies the region of interest on the basis of at least the second image out of the first image and the second image. In the eleventh aspect, in a case of capturing an in-vivo image is imaged, the classification unit can perform determination of the type of polyp (whether it is neoplastic or non-neoplastic), diagnosis of the stage of cancer, determination of the position in the lumen (imaging position), and the like as "classification".

The image processing device according to a twelfth aspect is the image processing device according to the eleventh aspect, further comprising a second output unit that outputs information indicating a result of the classification. In the twelfth aspect, the output of the information indicating a classification result can be performed by screen display, audio output, or the like, and thereby the user can easily recognize the classification result.

The image processing device according to a thirteenth aspect is the image processing device according to the twelfth aspect, in which the display control unit causes the display device to display the information indicating the result of the classification. In the thirteenth aspect, the display of the information can be performed by, for example, characters, numbers, figures, symbols, colors, or the like according to the classification result, and thereby the user can easily recognize the information on the region of interest. In addition, the information may be superimposed and displayed on the image or may be displayed separately from the image.

The image processing device according to a fourteenth aspect is the image processing device according to any one of the first to thirteenth aspects, in which the first observation light is white light including light in wavelength ranges of red, blue, and green, and the second observation light is narrow-band light corresponding to a wavelength range of any of red, blue, and green. According to the fourteenth aspect, it is possible to detect and classify the region of interest using the narrow-band light while continuously displaying and observing the first image (and the registered first image) captured with the white light. Narrow-band light corresponding to violet and infrared wavelength ranges may be used.

The image processing device according to a fifteenth aspect is the image processing device according to any one of the first to thirteenth aspects, in which the first observation light is first narrow-band light corresponding to a wavelength range of any of red, blue, and green, and the second observation light is a second narrow-band light corresponding to a wavelength range of any of red, blue, and green and having a wavelength range different from that of the first narrow-band light. The fifteenth aspect defines an aspect in which a plurality of narrow-band lights are used, and for example, a combination of a plurality of blue narrow-band lights having different wavelengths, a blue narrow-band light and a green narrow-band light, a plurality of red narrow-band lights having different wavelengths, and the like can be used, but the observation light is not limited to these combinations. Narrow-band light corresponding to violet and infrared wavelength ranges may be used.

The image processing device according to a sixteenth aspect is the image processing device according to any one of the first to fifteenth aspects, in which the image input unit inputs, as the second image, an image captured using light having a center wavelength shorter than that of the first observation light as the second observation light. As described above, since the structure of the subject reflected in the image varies depending on the wavelength of observation light, it is preferable to use observation light having a short wavelength in order to capture and detect a fine structure. In the sixteenth aspect, while continuing the observation by sequentially displaying the first image, it is possible to accurately detect the fine structure using the second image.

In order to achieve the above-described object, an endoscope system according to a seventeenth aspect of the present invention comprises the image processing device according to any one of the first aspect to the sixteenth aspect; the display device; an endoscope that has an insertion part to be inserted into a subject, the insertion part having a distal end rigid part, a bendable part connected to a proximal end side of the distal end rigid part, and a flexible part connected to a proximal end side of the bendable part, and has an operation part connected to a proximal end side of the insertion part; a light source device that irradiates the subject with the first observation light or the second observation light; and an imaging unit that has an imaging lens for forming an optical image of the subject and an imaging element on which the optical image is formed by the imaging lens, in which the imaging lens is provided on the distal end rigid part. According to the seventeenth aspect, in a case where an image is acquired using a plurality of observation lights, it is possible to observe an accurate structure of a subject while preventing a substantial decrease in a frame rate, and a user can use the second image for other purposes (such as detection and classification of the region of interest) while observing the first image sequentially displayed on the display device.

In the seventeenth aspect, light emitted from the light source may be directly used as observation light, or light generated by applying a filter that causes the light emitted from the light source to transmit a specific wavelength range may be used as the observation light. For example, in a case where narrow-band light is used as the first observation light and/or the second observation light, light irradiated from a light source for narrow-band light may be used as the observation light, or light generated by applying a filter that causes white light to transmit a specific wavelength range may be used as the observation light. In this case, different narrow-band lights may be irradiated at different timings by sequentially switching the filter applied to the white light.

In order to achieve the above-described object, an image processing method according to an eighteenth aspect of the present invention comprises an image input step of inputting a first image and a second image captured at different times, in which the first image captured with first observation light and the second image captured with second observation light different from the first observation light are input; a parameter calculation step of calculating a parameter for registering the first image and/or the second image to match the first image and the second image; an image generation step of applying the parameter to the first image to generate a registered first image; and a display control step of sequentially displaying the input first image and the generated registered first image on a display device. According to the eighteenth aspect, similarly to the first aspect, in a case where imaging is performed using a plurality of observation lights, it is possible to observe an accurate structure of a subject while preventing a substantial decrease in a frame rate.

The configuration of the eighteenth aspect may further include a configuration similar to that of the second to sixteenth aspects. In addition, a program for causing the endoscope system to execute the image processing method of these aspects and a non-transitory recording medium in which a computer-readable code of the program is recorded can also be mentioned as aspects of the present invention.

As described above, with the image processing device, the endoscope system, and the image processing method according to the embodiment of the present invention, in a case where imaging is performed using a plurality of observation lights, it is possible to observe an accurate structure of a subject while preventing a substantial decrease in the frame rate.

DESCRIPTION OF THE PREFERRED EMBODIMENTS

Hereinafter, an embodiment of an image processing device, an endoscope system, and an image processing method according to the embodiment of the present invention will be described in detail with reference to the accompanying drawings.

First Embodiment

Figure 1:
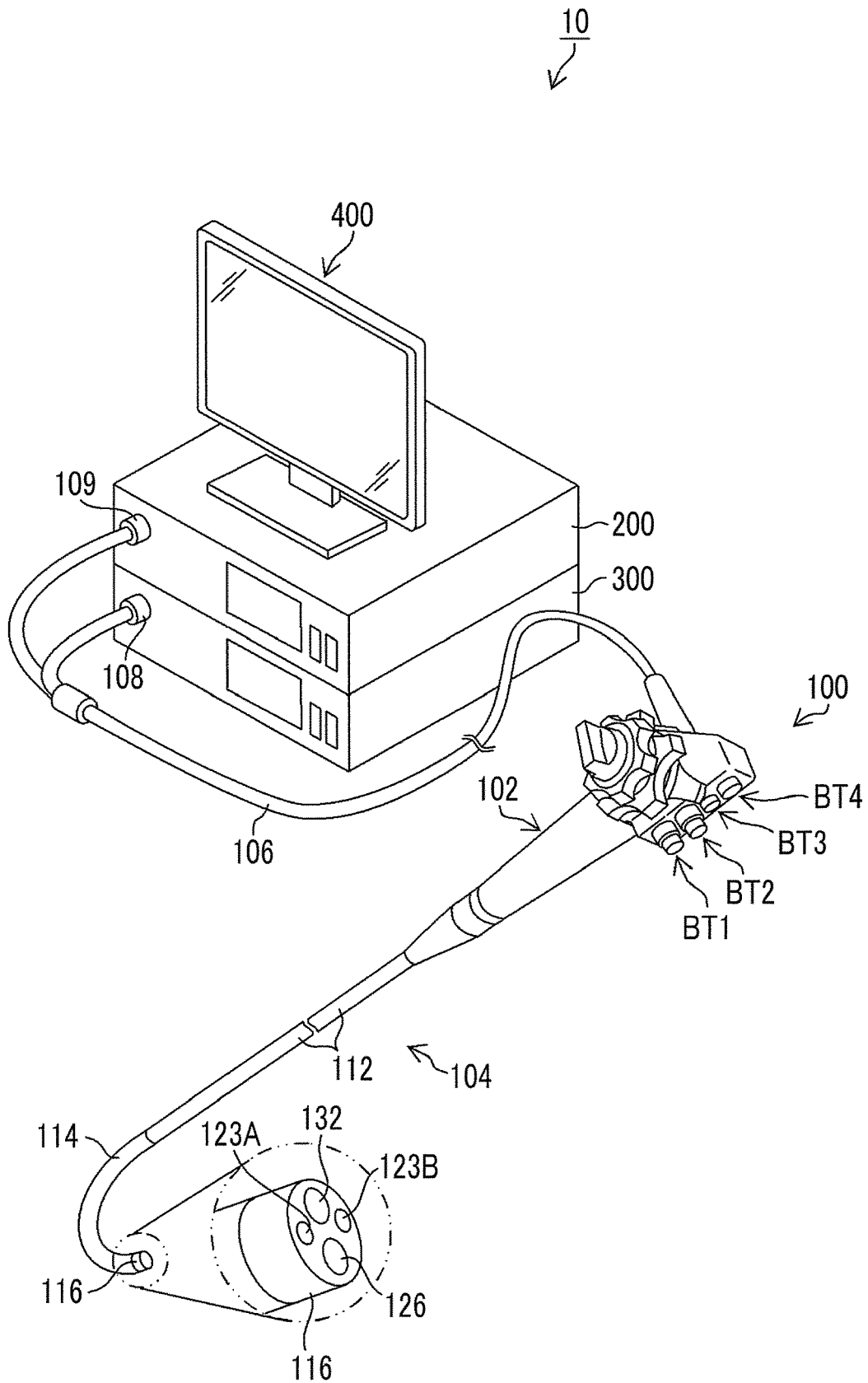
FIG. 1 is an external view illustrating an endoscope system according to a first embodiment.
Figure 2:
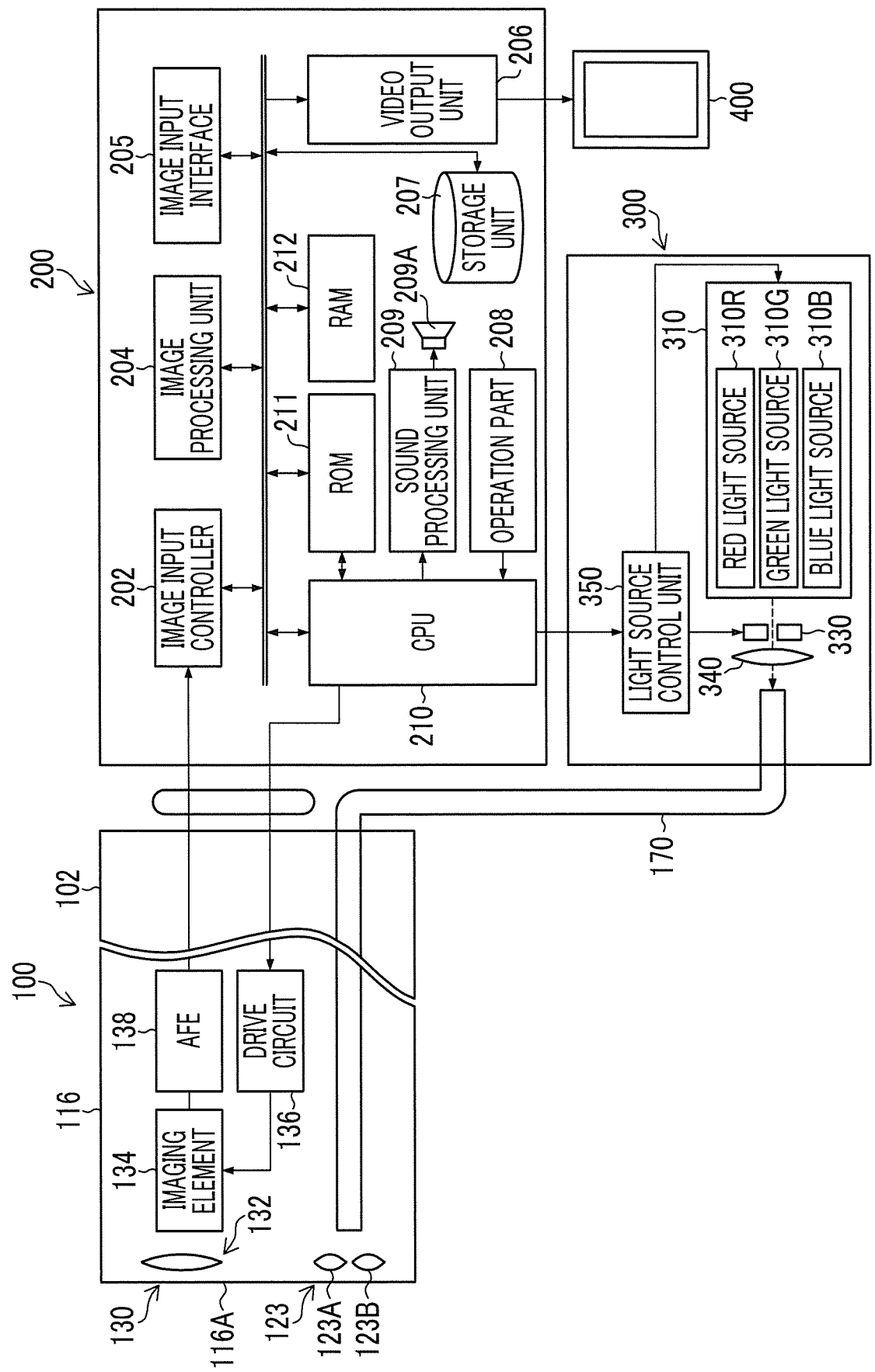
FIG. 2 is a block diagram showing a configuration of the endoscope system.

FIG. 1 is an external view showing an endoscope system 10 (image processing device, diagnosis support device, endoscope system, medical image processing device) according to the first embodiment, and FIG. 2 is a block diagram showing a configuration of the main part of the endoscope system 10. As shown in FIGS. 1 and 2, the endoscope system 10 is configured with an endoscope main body 100 (endoscope), a processor 200 (processor, image processing device, medical image processing device), a light source device 300 (light source device), and a monitor 400 (display device).

<Structure of Endoscope Main Body>

The endoscope main body 100 comprises a hand operation part 102 (operation part) and an insertion part 104 (insertion part) connected to the hand operation part 102. An operator (user) grasps and operates the hand operation part 102, and inserts the insertion part 104 into a body of a subject (living body) to observe the subject. In addition, the hand operation part 102 is provided with an air supply and water supply button BT1, a suction button BT2, a function button BT3 to which various functions are assigned, and an imaging button BT4 that receives an imaging instruction operation. The insertion part 104 is configured with a flexible part 112 (flexible part), a bendable part 114 (a bendable part), and a distal end rigid part 116 (distal end rigid part) in this order from the hand operation part 102 side. That is, the bendable part 114 is connected to a proximal end side of the distal end rigid part 116, and the flexible part 112 is connected to a proximal end side of the bendable part 114. The hand operation part 102 is connected to the proximal end side of the insertion part 104. A user can bend the bendable part 114 by operating the hand operation part 102 to change the direction of the distal end rigid part 116 vertically and horizontally. The distal end rigid part 116 is provided with an imaging optical system 130 (imaging unit), an illumination part 123, a forceps port 126, and the like (refer to FIGS. 1 to 3).

During observation and treatment, white light and/or narrow-band light (one or more of red narrow-band light, green narrow-band light, and blue narrow-band light) can be irradiated from illuminating lenses 123A and 123B of the illumination part 123 by operating an operation part 208 (refer to FIG. 2). In addition, by the operation of the air supply and water supply button BT1, cleaning water is discharged from a water supply nozzle (not shown), and an imaging lens 132 (imaging lens) and the illuminating lenses 123A and 123B of the imaging optical system 130 can be cleaned. A pipe line (not shown) is communicated with the forceps port 126 opened at the distal end rigid part 116, and a treatment tool (not shown) for tumor excision or the like is inserted into the pipe line and is appropriately moved forward and backward to perform a necessary treatment on the subject.

Figure 3:
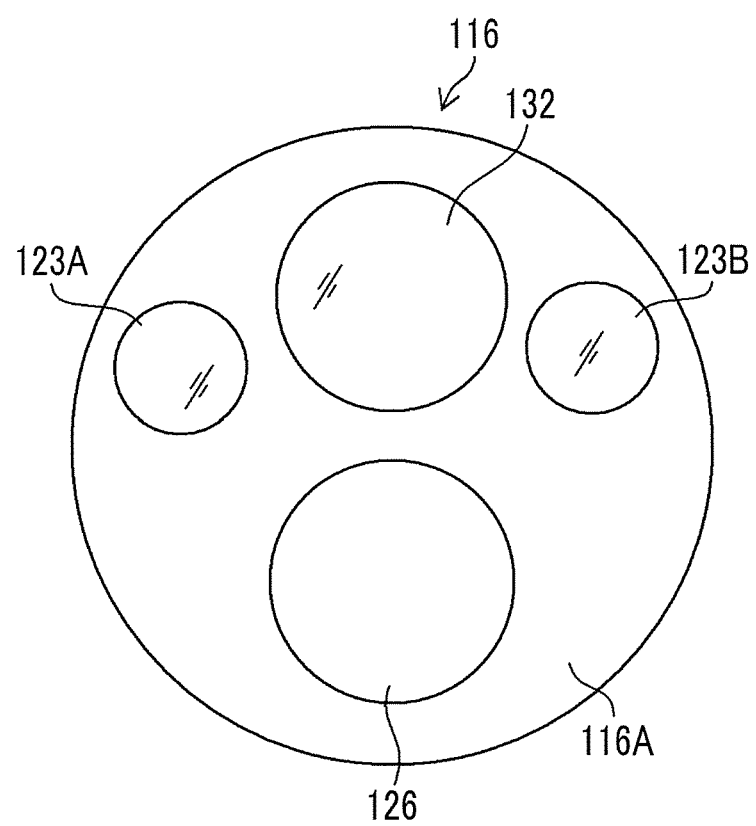
FIG. 3 is a diagram showing a configuration of a distal end rigid part of an endoscope.

As shown in FIGS. 1 to 3, the imaging lens 132 (imaging unit) is arranged on a distal end side end surface 116A of the distal end rigid part 116. A complementary metal-oxide semiconductor (CMOS) type imaging element 134 (an imaging element, an imaging unit), a drive circuit 136, and an analog front end 138 (AFE) are arranged at the back of the imaging lens 132, and an image signal is output by these elements. The imaging element 134 is a color image element and comprises a plurality of pixels composed of a plurality of light-receiving elements disposed in a matrix (a two-dimensional array) in a specific pattern array (a Bayer array, an X-Trans (registered trademark) array, a honeycomb array, or the like). Each pixel of the imaging element 134 includes a microlens, a red (R), green (G), or blue (B) color filter, and a photoelectric conversion part photodiode or the like). The imaging optical system 130 can generate a color image from pixel signals of three colors of red, green, and blue, or can generate an image from pixel signals of any one or two colors of red, green, and blue. In the first embodiment, a case where the imaging element 134 is a CMOS type imaging element will be described, but the imaging element 134 may be a charge coupled device (CCD) type imaging element. Each pixel of the imaging element 134 may further comprise a violet color filter corresponding to a violet light source and/or an infrared filter corresponding to an infrared light source.

An optical image of a subject (tumor part, lesion part) is formed on a light-receiving surface (imaging surface) of the imaging element 134 by the imaging lens 132, converted into an electric signal, output to the processor 200 via a signal cable (not shown), and converted into a video signal. As a result, an observation image is displayed on the monitor 400 connected to the processor 200.

In addition, the illuminating lenses 123A (for visible light) and 123B (for infrared light) of the illumination part 123 are provided adjacent to the imaging lens 132 on the distal end side end surface 116A of the distal end rigid part 116. At the back of the illuminating lenses 123A and 123B, an emission end of a light guide 170 described later is arranged, the light guide 170 is inserted into the insertion part 104, the hand operation part 102, and a universal cable 106, and an incident end of the light guide 170 is disposed in a light guide connector 108.

<Structure of Light Source Device>

As shown in FIG. 2, the light source device 300 is configured with a light source 310 for illumination, a stop 330, a condensing lens 340, a light source control unit 350, and the like, and causes observation light to enter the light guide 170. The light source 310 comprises a red light source 310R, a green light source 310G, and a blue light source 310B that perform irradiation of each of red, green, and blue narrow-band lights, and can perform irradiation of red, green, and blue narrow-band lights. The illuminance of the observation light by the light source 310 is controlled by the light source control unit 350, and the illuminance of the observation light can be lowered and the illumination can be stopped as necessary.

The light source 310 can emit red, green, and blue narrow-band lights in any combination. For example, white light (normal light) can be irradiated as observation light by simultaneously emitting red, green, and blue narrow-band lights or narrow-band light (special light) can be irradiated by emitting one or two of them. The light source 310 may further comprise the violet light source that performs irradiation of violet light (an example of narrow-band light) and the infrared light source that performs irradiation of infrared light (an example of narrow-band light). In addition, white light or narrow-band light may be irradiated as observation light by a light source that performs irradiation of white light and a filter that the white light and each narrow-band light are transmitted.

<Wavelength Range of Light Source>

The light source 310 may be a light source that generates light in a white range or light in a plurality of wavelength ranges as light in a white range, and alternatively may be a light source that generates light in a specific wavelength range narrower than a white wavelength range. The specific wavelength range may be a blue range or a green range of a visible range, or a red range in a visible range. In a case where the specific wavelength range is the blue range or the green range in the visible range, the specific wavelength range may include a wavelength range of 390 nm to 450 nm, or 530 nm to 550 nm, and may have a peak wavelength in a wavelength range of 390 nm to 450 nm, or 530 nm to 550 nm. In addition, in a case where the specific wavelength range is a red range in the visible range, the wavelength range may include a wavelength range of 585 nm to 615 nm, or 610 nm to 730 nm, and light in the specific wavelength range may have a peak wavelength in a wavelength range of 585 nm to 615 nm, or 610 nm to 730 nm.

The light of the specific wavelength range described above includes a wavelength range in which light absorption coefficients of oxygenated hemoglobin and reduced hemoglobin are different, and may have a peak wavelength in the wavelength range in which the light absorption coefficients of oxygenated hemoglobin and reduced hemoglobin are different. In this case, the specific wavelength range includes a wavelength range of 400±10 nm, 440±10 nm, 470±10 nm, or 600 nm to 750 nm, and may have a peak wavelength in a wavelength range of 400±10 nm, 440±10 nm, 470±10 nm, or 600 nm to 750 nm.

In addition, the light generated by the light source 310 includes a wavelength range of 790 nm to 820 nm or 905 nm to 970 nm, and may have a peak wavelength in a wavelength range of 790 nm to 820 nm or 905 nm to 970 nm.

The light source 310 may comprise a light source that performs irradiation of excitation light having a peak of 390 nm to 470 nm. In this case, an image for medical use (in-vivo image) having information on fluorescence emitted by a fluorescent material in the subject (living body) can be acquired. In a case of acquiring a fluorescent image, a coloring agent for a fluorescence method (such as fluorescein and acridine orange) may be used.

A light source type (a laser light source, a xenon light source, a light-emitting diode (LED) light source, and the like), a wavelength, presence or absence of a filter, and the like of the light source 310 are preferably configured according to a type of the subject, a purpose of observation, and the like. In addition, the wavelength of the observation light is preferably combined and/or switched according to a type of the subject, a purpose of observation, and the like. In a case where the wavelength is switched, the wavelength of the light to be irradiated may be switched by, for example, rotating a disk-shaped filter (a rotary color filter) that is disposed in front of the light source and provided with a filter that transmits or blocks light having a specific wavelength.

In addition, the imaging element used in carrying out the present invention is not limited to a color image pickup element in which a color filter is arranged for each pixel as in the imaging element 134, and may be a monochrome imaging element. In a case of using the monochrome imaging element, it is possible to capture an image in a frame-sequential (color-sequential) manner by sequentially switching the wavelength of observation light. For example, the wavelength of the emitted observation light may be sequentially switched among (blue, green, and red), or the wavelength of the observation light emitted by the rotary color filter (red, green, blue, and the like) may be switched through irradiation of broad-band light (white light). In addition, the wavelength of the observation light emitted by the rotary color filter (green, blue, or the like) may be switched through irradiation of one or a plurality of narrow-band lights (green, blue, or the like). The narrow-band light may be infrared light (first narrow-band light, second narrow-band light) having two or more different wavelengths.

By connecting the light guide connector 108 (refer to FIG. 1) to the light source device 300, observation light irradiated from the light source device 300 is transmitted to the illuminating lenses 123A and 123B via the light guide 170, and is irradiated from the illuminating lenses 123A and 123B to the observation range.

<Configuration of Processor>

A configuration of the processor 200 will be described on the basis of FIG. 2. The processor 200 inputs an image signal output from the endoscope main body 100 via an image input controller 202 and an image input interface 205, performs necessary image processing in an image processing unit 204, and outputs the image signal via a video output unit 206. As a result, an observation image (in-vivo image) is displayed on the monitor 400 (the display device). These processes are performed under the control of a central processing unit (CPU) 210. That is, the CPU 210 has functions as an image acquisition unit, a medical image acquisition unit, an image input unit, a parameter calculation unit, an image generation unit, a display control unit, an image correction unit, a detection unit, a classification unit, a first output unit, and a second output unit. A storage unit 207 stores an image of a subject (an image for medical use or a captured image), information indicating a result of detection and/or classification of a region of interest, and the like. Under the control of the CPU 210 and the image processing unit 204, a sound processing unit 209 outputs a message (sound) or the like according to the result of detection and/or classification of the region of interest from a speaker 209A.

A read only memory (ROM) 211 is a nonvolatile storage element (non-transitory recording medium), and stores a computer-readable code of a program for causing the CPU 210 and/or the image processing unit 204 (image processing device, and computer) to execute the image processing method according to the embodiment of the present invention. A random access memory (RAM) 212 is a storage element for temporary storage during various types of processing, and can also be used as a buffer during image acquisition.

<Function of Image Processing Unit>

Figure 4:
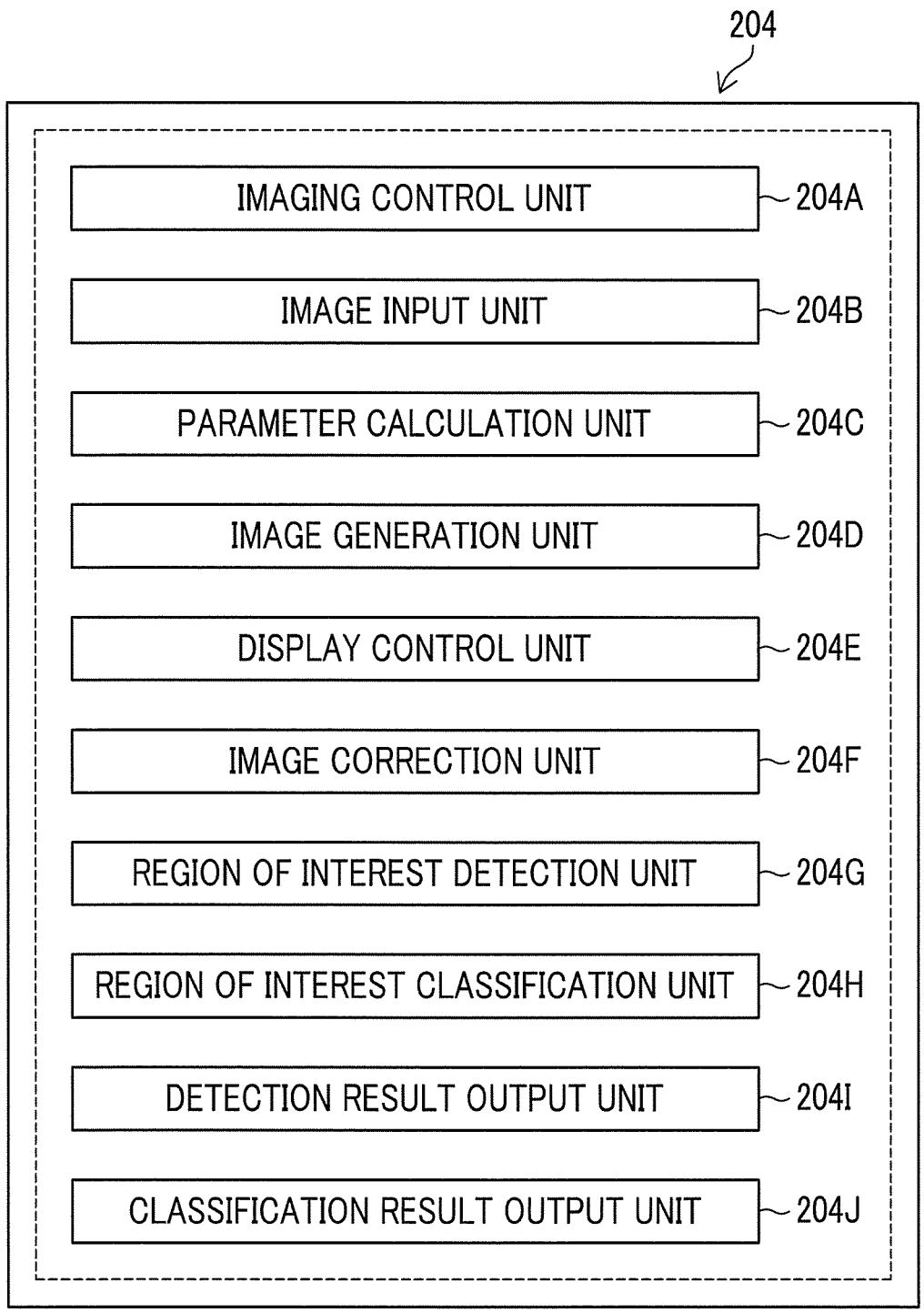
FIG. 4 is a diagram showing a functional configuration of an image processing unit.

FIG. 4 is a diagram showing a functional configuration of the image processing unit 204 (medical image acquisition unit, medical image analysis processing unit, a medical image analysis result acquisition unit). The image processing unit 204 has an imaging control unit 204A (image input unit), an image input unit 204B (image input unit), a parameter calculation unit 204C (parameter calculation unit), an image generation unit 204D (image generation unit), a display control unit 204E (display control unit), an image correction unit 204F (image correction unit), a region of interest detection unit 204G (detection unit), a region of interest classification unit 204H (classification unit), a detection result output unit 204I (first output unit), and a classification result output unit 204J (second output unit). The region of interest detection unit 204G and the region of interest classification unit 204H also operate as the medical image analysis processing unit.

The image processing unit 204 may comprise a special light image acquisition unit that acquires a special light image having information on a specific wavelength range on the basis of a normal light image obtained through irradiation of light in a white range or light of a plurality of wavelength ranges as light of a white range. In this case, the signal of the specific wavelength range can be obtained by calculation based on color information of RGB (R: red, G: green, B: blue) or CMY (C: cyan, M: magenta, Y: yellow) included in the normal light image.

The image processing unit 204 may comprise a feature quantity image generation unit that generates a feature quantity image by calculation based on at least one of a normal light image obtained through irradiation of light in a white range or light in a plurality of wavelength ranges as light in a white range or a special light image obtained through irradiation of light in a specific wavelength range, and may acquire and display the feature quantity image as an image for medical use (medical image).

Details of the processing by these functions of the image processing unit 204 will be described later. The processing by these functions is performed under the control of the CPU 210.

The function of the image processing unit 204 described above can be realized by using various processors. The various processors include, for example, a central processing unit (CPU) that is a general-purpose processor that executes software (program) to realize various functions. In addition, the above-described various processors include a programmable logic device (PLD) which is a processor whose circuit configuration can be changed after manufacturing, such as a graphics processing unit (GPU) and a field programmable gate array (FPGA) which are processors specialized for image processing. Further, the above-described various processors also include a dedicated electric circuit which is a processor having a dedicated circuit configuration for executing specific processing such as an application specific integrated circuit (ASIC).

The function of each unit may be realized by one processor, or may be realized by a plurality of processors of the same type or different types (for example, a plurality of FPGAs, a combination of a CPU and an FPGA, or a combination of a CPU and a GPU). In addition, a plurality of functions may be realized by one processor. As a first example in which the plurality of functions are configured by one processor, there is an aspect in which one processor is configured by a combination of one or more CPUs and software, and the processor is realized as the plurality of functions, as represented by a computer such as an image processing device main body or a server. As a second example, there is an aspect in which a processor for realizing the functions of the entire system by one integrated circuit (IC) chip as represented such as a system on chip (SoC) is used. In this way, various functions are configured by using one or more of the above-described various processors as a hardware structure. More specifically, the hardware structure of these various processors is an electrical circuitry where circuit elements, such as semiconductor elements, are combined.

In a case where the above-described processor or electric circuit executes software (program), a processor (computer) readable code of the software to be executed is stored in a non-transitory recording medium such as a read only memory (ROM), and the processor refers to the software. The software stored in the non-transitory recording medium includes a program for inputting an image and measuring a subject. The code may be recorded on a non-transitory recording medium such as various types of magneto-optical recording device or a semiconductor memory instead of the ROM. In the processing using the software, for example, a random access memory (RAM) is used as a temporary storage region, and for example, data stored in an electronically erasable and programmable read only memory (EEPROM) (not shown) can be referred to.

<Structure of Operation Part>

The processor 200 comprises the operation part 208. The operation part 208 comprises an operation mode setting switch (not shown) and the like, and a user can set the wavelength of the observation light (whether white light or narrow-band light is used, and which narrow-band light is used in a case of the narrow-band light) via the operation part 208. In addition, the operation part 208 includes a keyboard and a mouse (not shown), and the user can perform a setting operation of an imaging condition and a display condition via these devices. These setting operations may be performed via a foot switch (not shown), or may be performed by voice, line of sight, gesture, or the like. The operation mode may be set by assigning an operation mode setting function to the function button BT3 (refer to FIG. 1) of the hand operation part 102 as described above.

<Configuration of Storage Unit>

The storage unit 207 (recording device) is configured to include various types of magneto-optical recording medium and non-transitory recording media such as a semiconductor memory, and stores a captured image (first image and second image), a registered first image, information indicating a region of interest, information indicating a classification result of the region of interest, and the like in association with each other. These images and information are displayed on the monitor 400 by an operation via the operation part 208 and control of the CPU 210 and/or the image processing unit 204.

In addition to the above-described images, an analysis result of a region of attention (region of interest) that is a region to be noticed included in an image for medical use (medical image) and one or both of the presence or absence of an aspect to be noticed may be stored in the storage unit 207 (recording device). In this case, the image processing unit 204 (medical image analysis processing unit, the medical image analysis result acquisition unit) can acquire the analysis result from the storage unit 207 and display the analysis results on the monitor 400.

<Configuration of Display Device>

The monitor 400 (display device) displays the first image, the second image, the registered first image, the imaging condition setting screen, the display condition setting screen, information indicating the detection result of the region of interest, information indicating the classification result of the region of interest, and the like by an operation via the operation part 208 and under the control of the CPU 210 and/or the image processing unit 204. In addition, the monitor 400 has a touch panel (not shown) for performing an imaging condition setting operation and/or a display condition setting operation.

<Image Processing Method>

Figure 5:
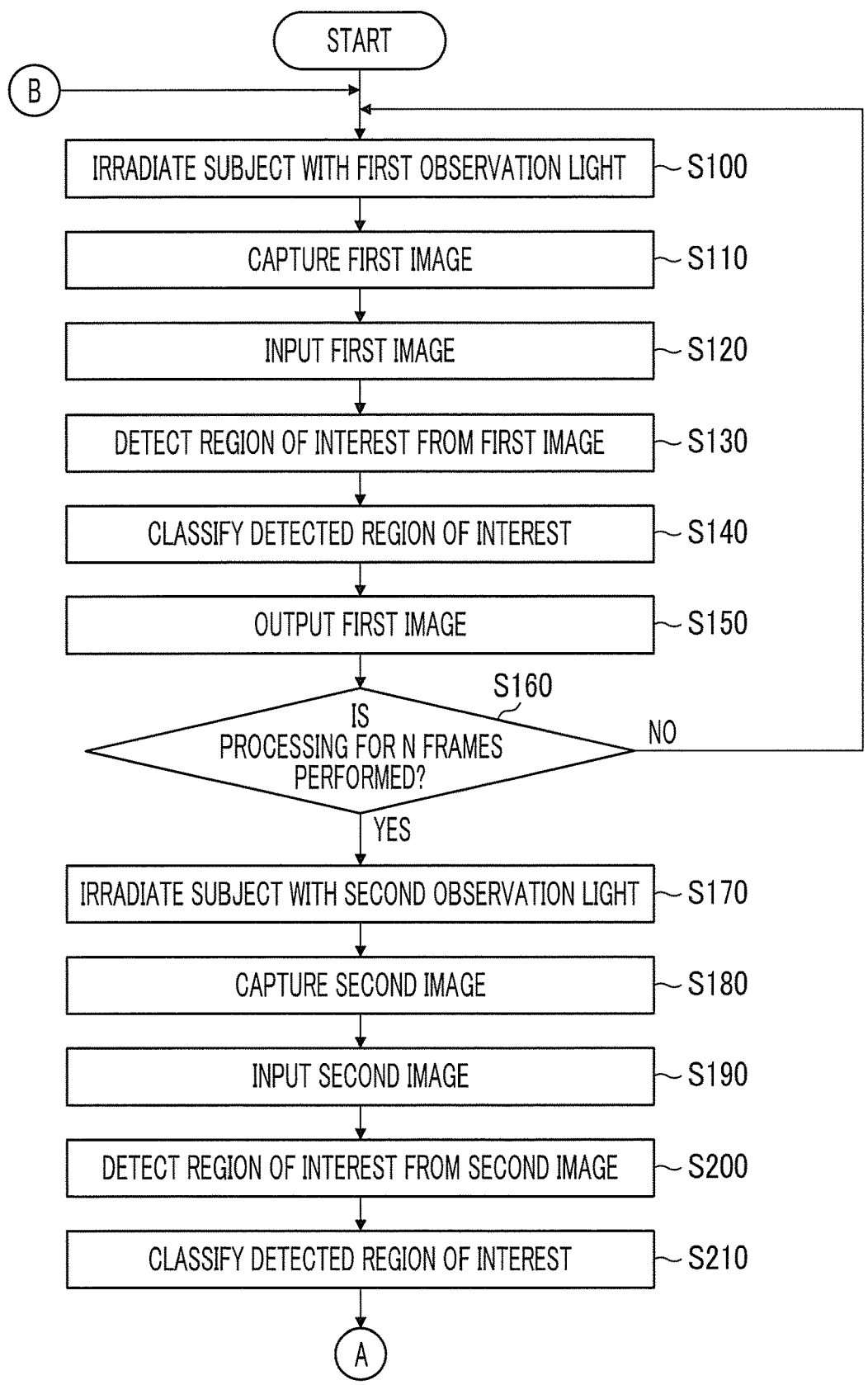
FIG. 5 is a flowchart showing processing of an image processing method.
Figure 6:
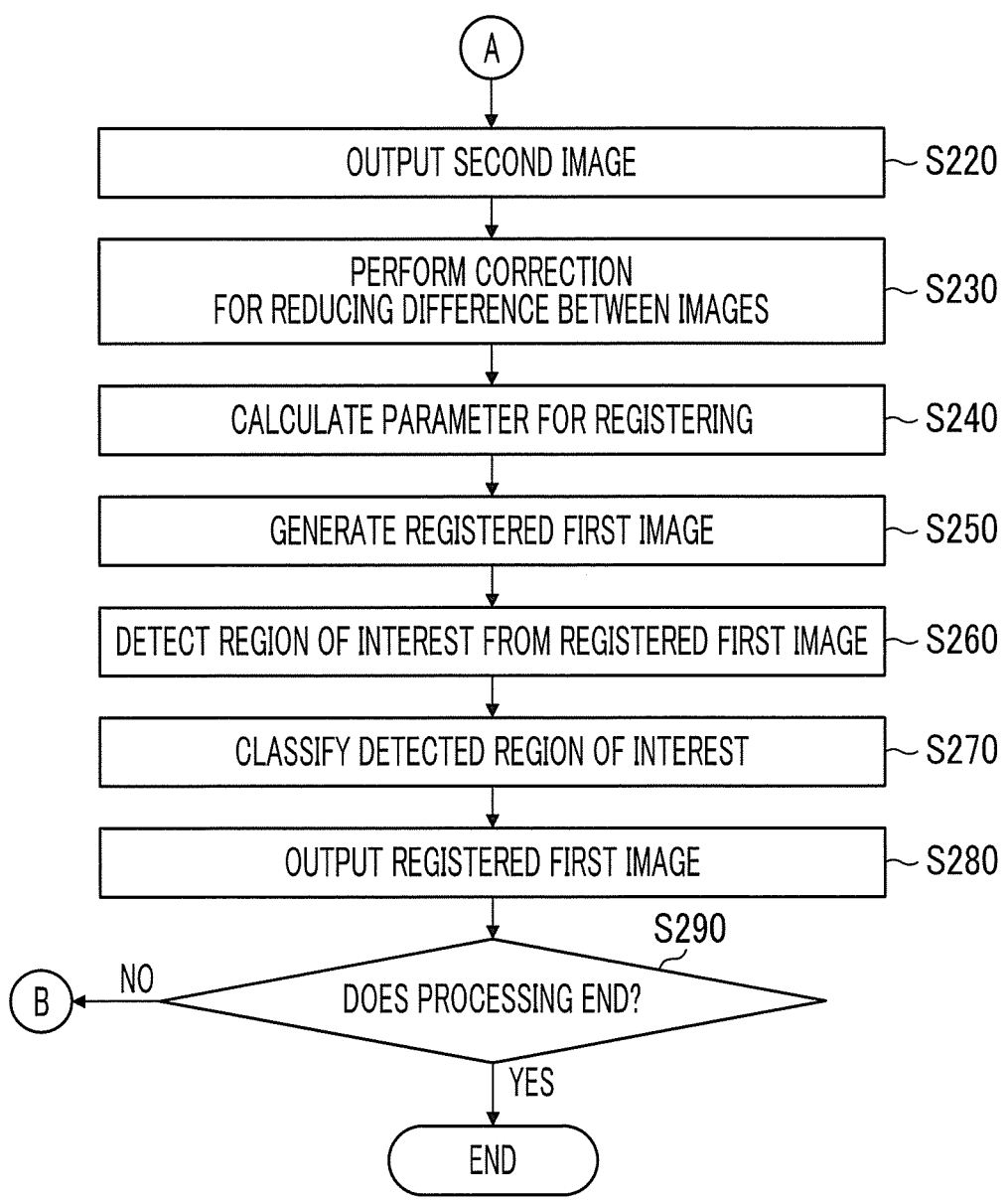
FIG. 6 is a flowchart (continued from FIG. 5) showing processing of the image processing method.

The image processing method using the endoscope system 10 will be described. FIGS. 5 and 6 are flowcharts showing the processing of the image processing method according to the first embodiment.

<Observation Light of First Image and Second Image>

In the first embodiment, a case will be described in which a white light image (normal image) using white light as observation light (first observation light) is acquired as a first image, and a blue light image (special light image) using blue light (center wavelength is shorter than the first observation light) as narrow-band light as observation light (second observation light) is acquired as a second image. However, the observation light in the present invention is not limited to such a combination. For example, the second image may be a special light image acquiring green light, red light, infrared light, violet light, or the like as narrow-band light as observation light. In addition, the first image and the second image may be acquired by using both the first observation light and the second observation light as narrow-band light (for example, first narrow-band light and second narrow-band light such as blue light and green light, or red light having different wavelengths). In the first embodiment, only the first observation light or only the second observation light is irradiated in one frame to capture the first image and the second image.

<Imaging Pattern of First Image and Second Image>

Figure 7A:
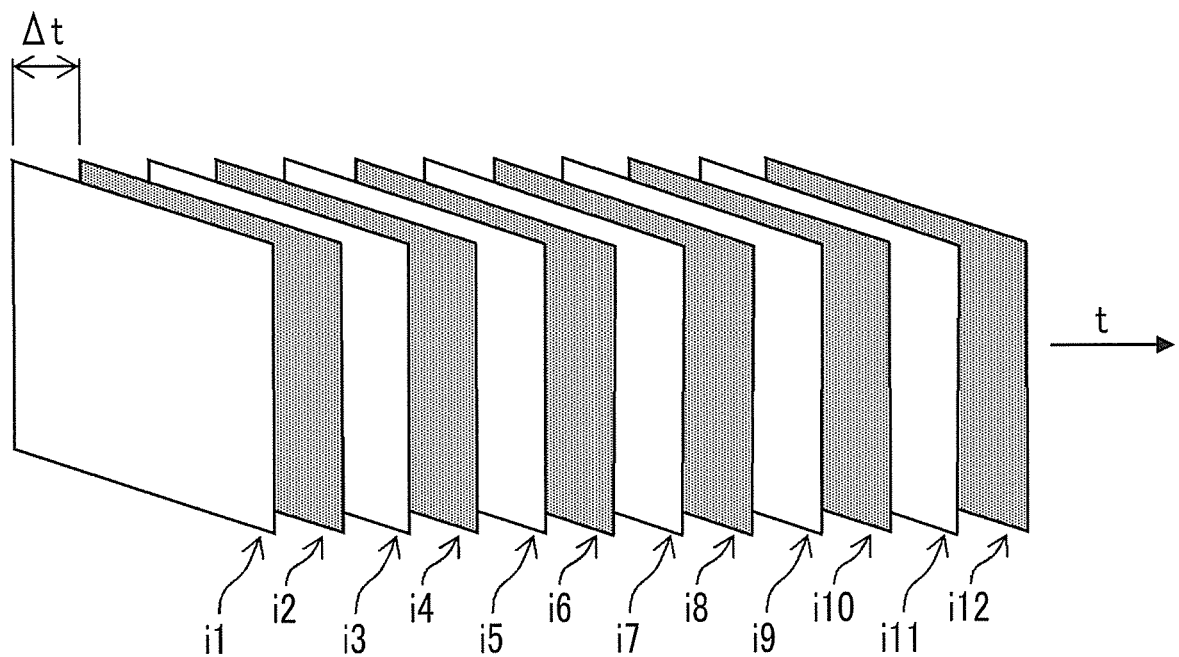
FIGS. 7A and 7B are diagrams showing examples of acquisition patterns of a first image and a second image.
Figure 7B:
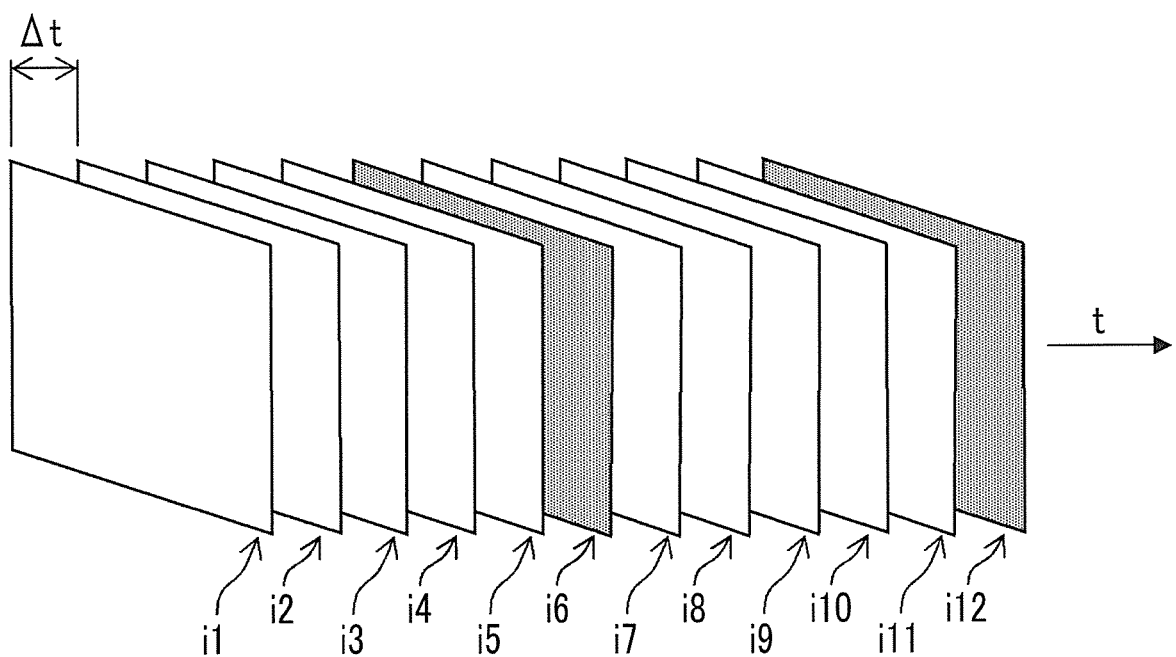

FIGS. 7A and 7B are diagrams showing examples of acquisition patterns of a first image and a second image according to the first embodiment. FIG. 7A shows a pattern in which the first observation light (white light, normal light) and the second observation light (blue narrow-band light, special light) are alternately irradiated at a specified frame rate (frame interval: Δt) such as 30 frames or 60 frames per second, and thereby white light images (images i1, i3, i5, i7, i9, and i11) and blue light images (images i2, i4, i6, i8, i10, and i12) are alternately obtained. The white light image and the blue light image are images captured at different times. On the other hand, FIG. 7B shows a pattern in which five white light images (images i1 to i5, and i7 to i11) are captured through irradiation of the first observation light (white light, normal light) for five frames in succession, and then the second observation light (blue narrow-band light, special light) is irradiated in one frame to capture one blue light image (images i6, and i12). Also in this pattern, the white light image and the blue light image are images captured at different times. These imaging patterns can be set by the imaging control unit 204A due to a user operation via the operation part 208.

<Processing for First Image>

The CPU 210 and the imaging control unit 204A control the light source control unit 350 on the basis of the above-described imaging pattern to cause the red light source 310R, the green light source 310G, and the blue light source 310B to emit light, and then irradiate the subject with white light (first observation light) (step S100: imaging step, image input step), and captures an image (first image) of the subject by the imaging optical system 130, the imaging element 134, and the like (step S110: imaging step, image input step). The image input unit 204B inputs the captured image via the image input controller 202 and the image input interface 205 (step S120: image input step).

<Detection of Region of Interest>

The region of interest detection unit 204G detects a region of interest from the input (acquired) first image (step S130: region of interest detection step). The region of interest can be detected by the region of interest detection unit 204G comprising, for example, a known computer aided diagnosis (CAD) system. Specifically, it is possible to extract a region of interest (a region of attention that is a region to be noticed) and the presence or absence of a target (target to be noticed) in the region of interest on the basis of, for example, a feature quantity of a pixel of ab image for medical use. In this case, the region of interest detection unit 204G divides a detection target image into, for example, a plurality of rectangular regions, and sets each of the divided rectangular regions as a local region. The region of interest detection unit 204G calculates a feature quantity (for example, hue) of a pixel in the local region for each local region of the detection target image, and determines a local region having a specific hue from among the local regions as a region of interest.

<Detection of Region of Interest on the Basis of Deep Learning Algorithm>

The region of interest may be detected using a result of deep learning. For example, each time a new image is stored in the storage unit 207 (or each time a new image is captured), the region of interest detection unit 204G performs image analysis processing using deep learning on the basis of a deep learning algorithm to analyze whether or not the image includes a region of interest. As the deep learning algorithm, a known convolutional neural network method, that is, an algorithm for recognizing whether or not a region of interest is included in the image through repetition of a convolutional layer and a pooling layer, a fully connected layer, and an output layer can be used. In the image analysis processing using the deep learning, a learning device generated by giving an image labeled as "being a region of interest" or "not being a region of interest" as teacher data may be used. "Whether or not to perform such machine learning" and/or "whether or not to use a learning result" may be set according to a user's operation via the operation part 208 and the monitor 400.

Examples of the region of interest (region of attention) detected in step S130 include polyps, cancers, diverticula of the large intestine, inflammations, treatment scars (endoscopic mucosal resection (EMR) scar, endoscopic submucosal dissection (ESD) scar, clip portions, and the like), bleeding points, perforations, vascular atypia, and the like.

<Classification of Region of Interest>

The region of interest classification unit 204H classifies the region of interest detected in step S130 (step S140: region of interest classification step). Examples of classification include classification of polyp (neoplastic or non-neoplastic), diagnosis of the stage of cancer, current location in the lumen (pharynx, esophagus, stomach, duodenum, or the like in the upper part, cecum, ascending colon, transverse colon, descending colon, sigmoid colon, rectum, or the like in the lower part), and the like. Also in these classifications, the result of machine learning (deep learning) can be used as in the case of detection. The classification of the region of interest may be performed integrally with the detection.

<Output for First Image>

The display control unit 204E, the detection result output unit 204I, and the classification result output unit 204J output the white light image (first image) (step S150: first output step, second output step). The output can be performed by the display control unit 204E, the detection result output unit 204I, and the classification result output unit 204J displaying the white light image (first image), the information indicating the detection result, and the information indicating the classification result on the monitor 400 (display control step, first output step, and second output step). In addition, these pieces of information are stored in the storage unit 207 (first output step and second output step), whereby output can be performed. The information indicating the detection result and/or the classification result of the region of interest may be notified by voice via the sound processing unit 209 and the speaker 209A (first output step, second output step). The output of these aspects enables the user to easily recognize the region of interest, the detection result and the classification result thereof. A display example of the first image will be described later (refer to FIGS. 9 to 12). In addition, in the first embodiment, the frame in which the region of interest is detected may be recorded as a still image while continuously recording the first image (and the later-described registered first image) as a moving image.

The CPU 210 and the image processing unit 204 repeat processing of steps S100 to S150 for N frames (until YES in step S160). N is an integer of 1 or more, and is 1 in a case of the pattern of FIG. 7A, and 5 in a case of the pattern of FIG. 7B.

<Processing for Second Image>

As described above, in a case where image acquisition by the first observation light is performed for N frames, the determination in step S160 becomes YES, and the process proceeds to step S170. As a result, image acquisition by the second observation light is performed. In the first embodiment, the second observation light can be narrow-band light (for example, blue narrow-band light) having a center wavelength shorter than that of the first observation light (white light, normal light).

The processing for the second image can be performed in the same manner as the case of the first observation light. Specifically, the processing of steps S170, S180, S190, S200, S210, and S220 (imaging step, image input step, display control step, detection step, classification step, first output step, second output step) can be performed by each unit (imaging control unit 204A, region of interest detection unit 204G, and the like) of the image processing unit 204 in the same manner as steps S100 to S150. In a case where the second observation light is blue light (having a center wavelength shorter than that of white light), since a structure such as a fine blood vessel is depicted with high contrast in the second image, the region of interest can be detected and classified with high accuracy. The second image, and the detection result and the classification result for the second image can be output (displayed, stored, or the like) as necessary (for example, in a case where there is an instruction input from a user via the operation part 208, in a case where a region of interest that satisfies a specified condition is detected, or the like) (step S220).

<Processing for Registered First Image>

In the first embodiment, since only the first observation light or the second observation light is irradiated as the observation light and the first observation light and the second observation light are not simultaneously irradiated, the first image is not obtained at an irradiation timing of the first observation light. Therefore, in the first embodiment, the "registered first image" ("the first image at a capturing time of the second image, which is generated by applying a parameter for registering to the first image") is generated and displayed as follows, thereby preventing a substantial decrease in the frame rate of the first image.

<Image Used for Generating Registered First Image>

In order to generate the registered first image, for example, as in an image i5 (an example of the first image) and an image i6 (an example of the second image) in FIGS. 7A and 7B, a first image (image i5) acquired before a loss timing of the first image (an imaging timing of the image i6 that is the second image) can be used. In addition to such a pattern, for example, a plurality of first images (for example, images i4 and i5 in FIG. 7B) captured at different times may be used to generate the registered first image, or a first image (for example, an image i7 in FIG. 7B) acquired after the loss timing of the first image may be used. However, in a case of using a first image captured at a capturing time after the capturing time of the second image, there is a possibility that generation and display of the registered first image are delayed depending on a time difference between the capturing times. In addition, in a case where the time difference between the capturing times exceeds the threshold value, there is a possibility that an imaging range, an imaging angle, and the like change due to the movement of the subject or the like, and registering accuracy decreases.

Under such circumstances, in the generation of the registered first image, it is preferable to acquire the first image captured at a capturing time which is before a capturing time of the second image and at which a time difference from the capturing time of the second image is equal to or less than a threshold value. Accordingly, it is possible to generate the registered first image in which the time delay is small and a change in a tint and a structure of the subject between frames is small. The threshold value with respect to the capturing time can be determined according to the registering accuracy, an allowable time with respect to a delay in the generation and display of the image, and the like. In the following, a case in which the registered first image is generated using the image i5 as the first image and the image i6 as the second image will be described.

<Correction Before Registration (Pre-Processing)>

Figure 8A:
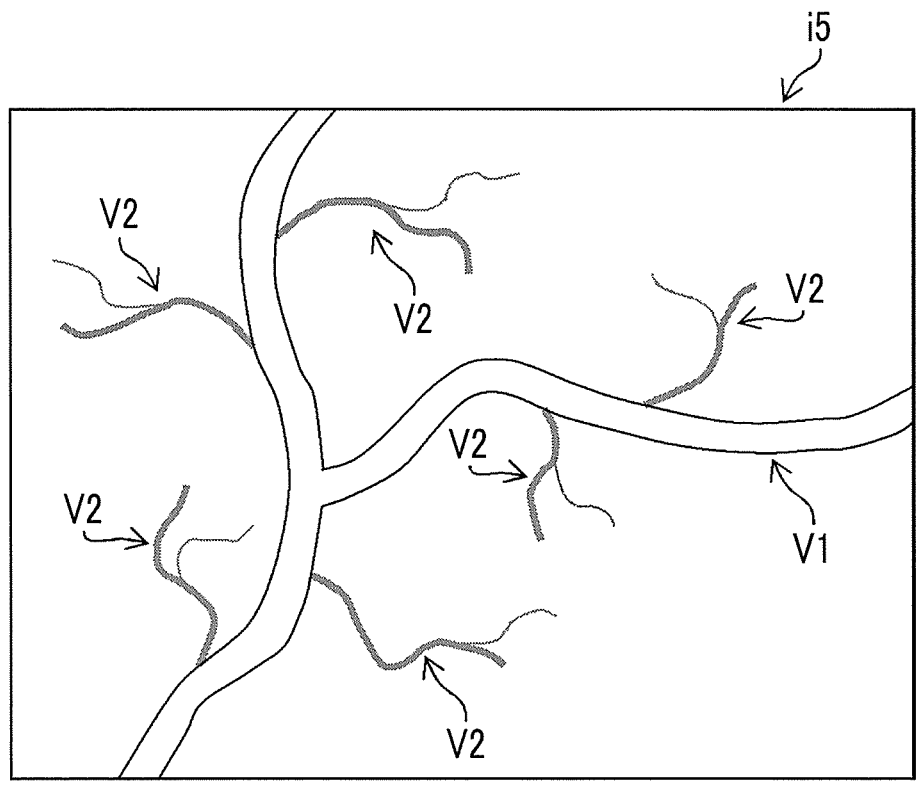
FIGS. 8A and 8B are diagrams showing examples of the first image and the second image.
Figure 8B:
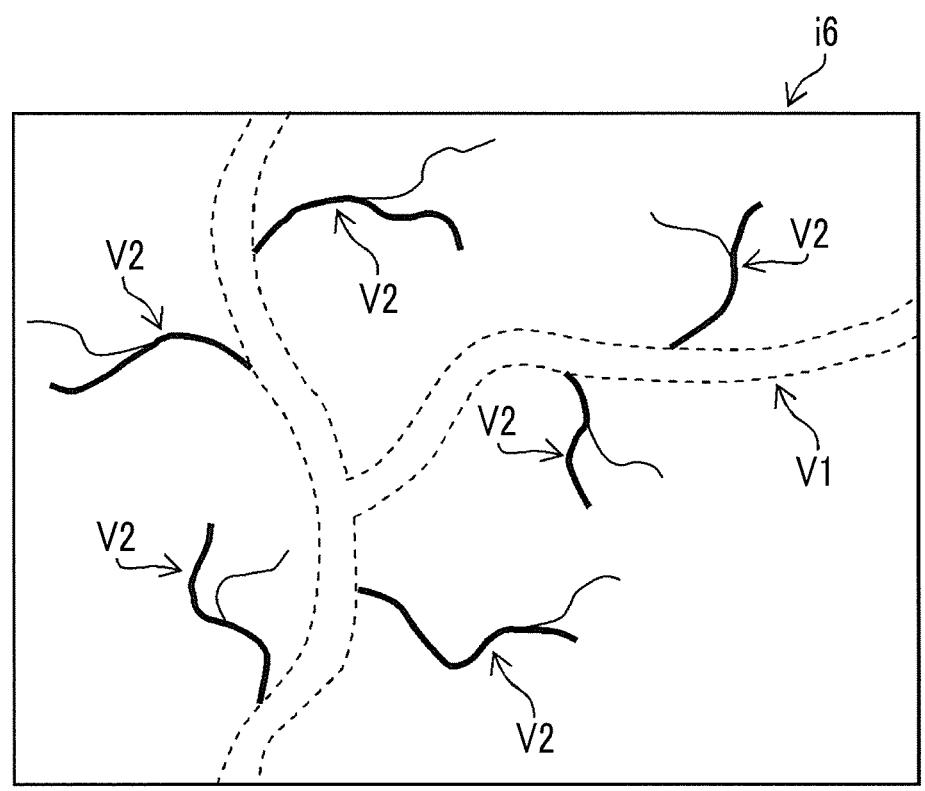

The wavelength of the observation light is different between the first image and the second image in addition to the imaging timing. As a result, in the first image (image i5) in which white light is used as the observation light, for example, as shown in FIG. 8A, a thick blood vessel V1 is clearly reflected, but a fine blood vessel V2 is not clearly reflected. On the other hand, in the second image (image i6) in which the blue narrow-band light is used as the observation light, for example, as illustrated in FIG. 8B, the thick blood vessel V1 is unclear compared to the first image, but the fine blood vessel V2 is clearly reflected. Therefore, in the first embodiment, the image processing unit 204 (image correction unit 204F) performs correction (pre-processing) for reducing a difference between the first image and the second image due to a difference between the first observation light and the second observation light (step S230: image correction step).

Figure 9:
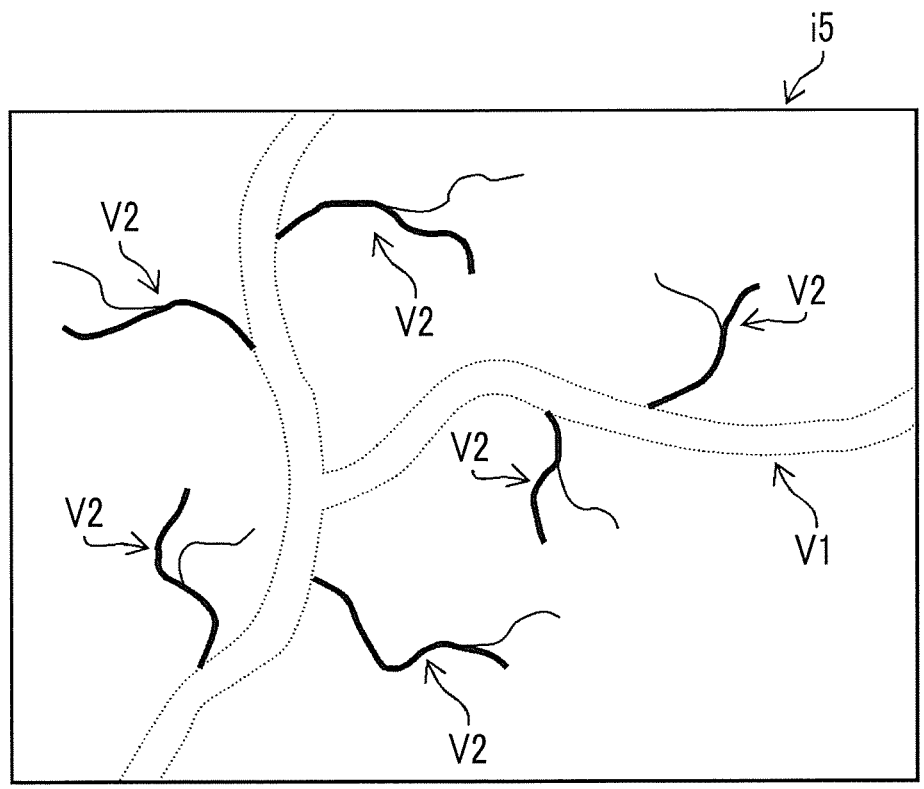
FIG. 9 is a diagram showing an example of a first image in which a common wavelength component is weighted.

Specifically, the image correction unit 204F extracts a component of a wavelength common to the first observation light and the second observation light from the image signal of the first image and the image signal of the second image, weights the extracted component of the wavelength to at least one of the image signal of the first image or the image signal of the second image, and generates an image in which the signal intensity of the component of the common wavelength is relatively stronger than the signal intensity of other components other than the component of the common wavelength. In the first embodiment, since the first observation light is white light and the second observation light is blue light, the image correction unit 204F increases the weight of the component of the blue light having the common wavelength between the image signal of the first image and the image signal of the second image. FIG. 9 is an example showing a state in which the blue light component is weighted in the image i5 (first image), and the fine blood vessel V2 is relatively emphasized.

In the first embodiment, it is possible to improve the registering accuracy by such a correction (pre-processing) and obtain the image (registered first image) in which the tint and the structure of the subject are small between frames. Instead of weighting the common wavelength component (blue light component) as described above, the registered first image may be generated using only the common wavelength component.

<Calculation and Registration of Parameters>

Figure 10:
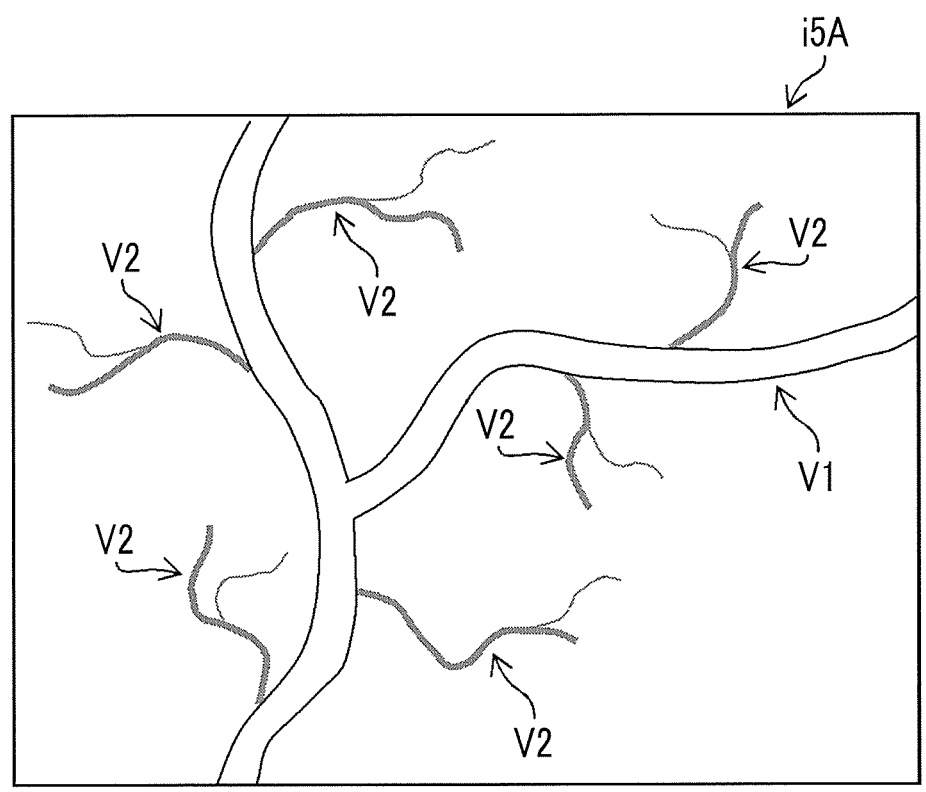
FIG. 10 is a diagram showing an example of a registered first image in which the weighting of the common wavelength component is returned to the original.

The parameter calculation unit 204C calculates a parameter for matching the corrected (pre-processing) image i5 (first image) and the image i6 (second image) by registration (step S240: parameter calculation step). The calculated parameter is a parameter for at least one of relative movement, rotation, or deformation, and the "deformation" may include enlargement or reduction. The image generation unit 204D applies the generated parameter to the corrected first image (image i5) to generate the registered first image (step S250: image generation step). In steps S240 and S250, the parameter calculation unit 204C calculates a parameter for performing projective transformation between the first image and the second image, and the image generation unit 204D performs projective transformation on the first image on the basis of the calculated parameter to generate the registered first image. FIG. 10 shows an example of the registered first image (image i5A). As described above, although the second image is used in the parameter calculation, since the registered first image is generated by moving or deforming the first image, the tint of the registered first image is not changed by the influence of the pixel value of the second image.

<Detection and Classification of Region of Interest>

The region of interest detection unit 204G detects a region of interest from the generated registered first image (step S260: region of interest detection step). In addition, the region of interest classification unit 204H classifies the detected region of interest detection unit (step S270: region of interest classification step). The detection and classification of the region of interest can be performed in the same manner as described above for steps S130 and S140, and the detection and classification may be performed integrally.

<Output for Registered First Image>

The display control unit 204E, the detection result output unit 204I, and the classification result output unit 204J output the registered first image (step 280: display control step, first output step, and second output step). The output of the registered first image can be performed by the display control unit 204E, the detection result output unit 204I, and the classification result output unit 204J displaying the registered first image, the information indicating the detection result of the region of interest, and the information indicating the classification result of the region of interest on the monitor 400 in the same manner as described above for the first image (display control step, first output step, and second output step). In addition, these pieces of information are stored in the storage unit 207 (first output step and second output step), whereby output can be performed. The output of the registered first image can be sequentially performed after the output of the first image. For example, the display control unit 204E repeats a display of the first image of N frames and a display of the registered first image of one frame (sequential display). Such sequential display may be performed in real time during the examination of the subject, or may be performed in a case where the first image and the registered first image are stored in the storage unit 207 and a user looks back the images later. Assuming that the above-described correction (weighting of the blue light component) is performed on the first image to generate the registered first image, in a case where the registered first image is output (displayed or the like), the image correction unit 204F may restore the balance of the wavelength component to the original state to make the registered first image the same as the white light. As a result, it is possible to prevent the user from feeling uncomfortable due to images having different wavelength balances being displayed on the monitor 400.

As described above, in the first embodiment, in addition to the normal display of the first image (step S150), the registered first image can be displayed even at a timing at which the first image cannot be acquired by the acquisition of the second image (step S280). This prevents a substantial decrease in the frame rate of the first image, and the user can continue observation with the normal light image (first image) captured by normal light (white light).

<Output for Region of Interest>

In the output of the first image and the registered first image (steps S150 and S280), the display control unit 204E, the detection result output unit 204I, and the classification result output unit 204J can output the information indicating the detection result of the region of interest and/or the information indicating the classification result of the region of interest in a case where the region of interest is detected from the first image and/or the registered first image. The information can be output by the display control unit 204E, the detection result output unit 204I, and the classification result output unit 204J displaying the information indicating the region of interest (for example, position and size of the region of interest) and/or the information indicating the classification result (for example, type of the region of interest, classification of the polyp, diagnosis of the stage of cancer, and the like) by characters, numbers, symbols, colors, and the like, in the same manner as described above for steps S130 and S140. These pieces of information may be superimposed and displayed on the first image and/or the registered first image.

Figure 11A:
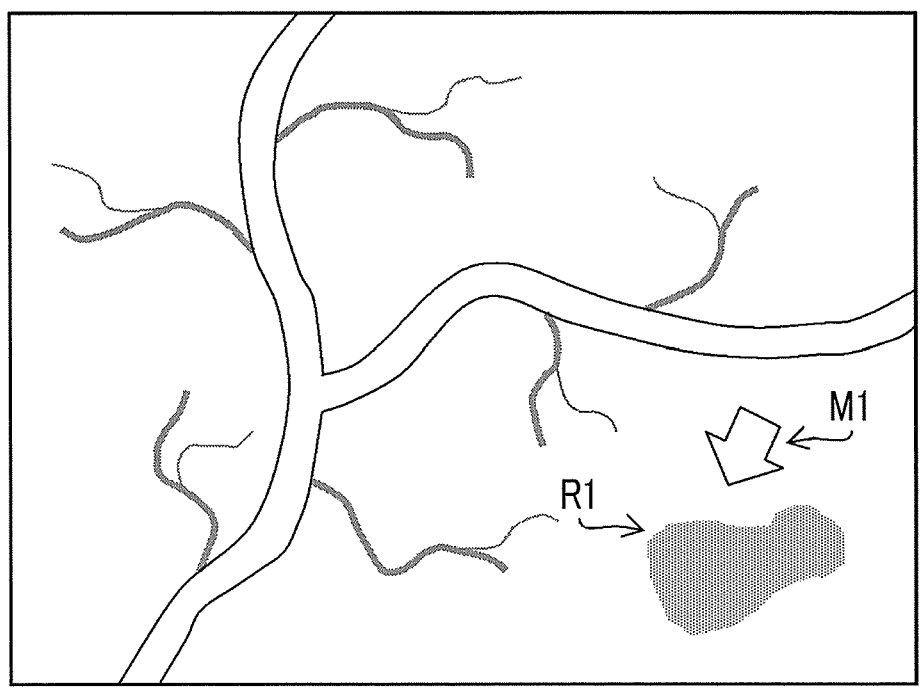
FIGS. 11A and 11B are diagrams showing display examples of the first image and the registered first image.
Figure 11B:
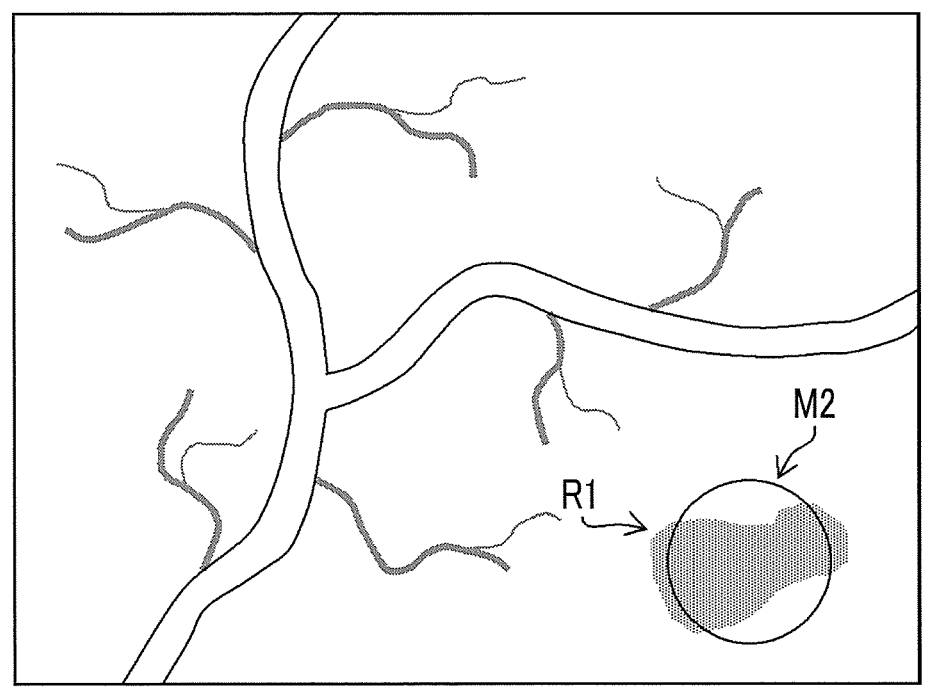

FIGS. 11A and 11B are diagrams showing display examples of information on a region of interest. FIG. 11A shows a state in which a symbol (arrow M1) indicating the position of the region of interest R1 sis superimposed and displayed on the image. In addition, FIG. 11B shows a state in which a marker M2 (for example, a circle corresponding to a diameter of 5 mm) for measuring the size of the region of interest R2 is superimposed and displayed on the image.

In addition to or instead of the display on the monitor 400, the detection result output unit 204I and the classification result output unit 204J may output the information indicating the detection result and/or the information indicating the classification result as sound by the sound processing unit 209 and the speaker 209A. Further, the detection result output unit 204I and the classification result output unit 204J may store information indicating the detection result and/or information indicating the classification result in the storage unit 207.

<Output for Second Image>

Figure 12:
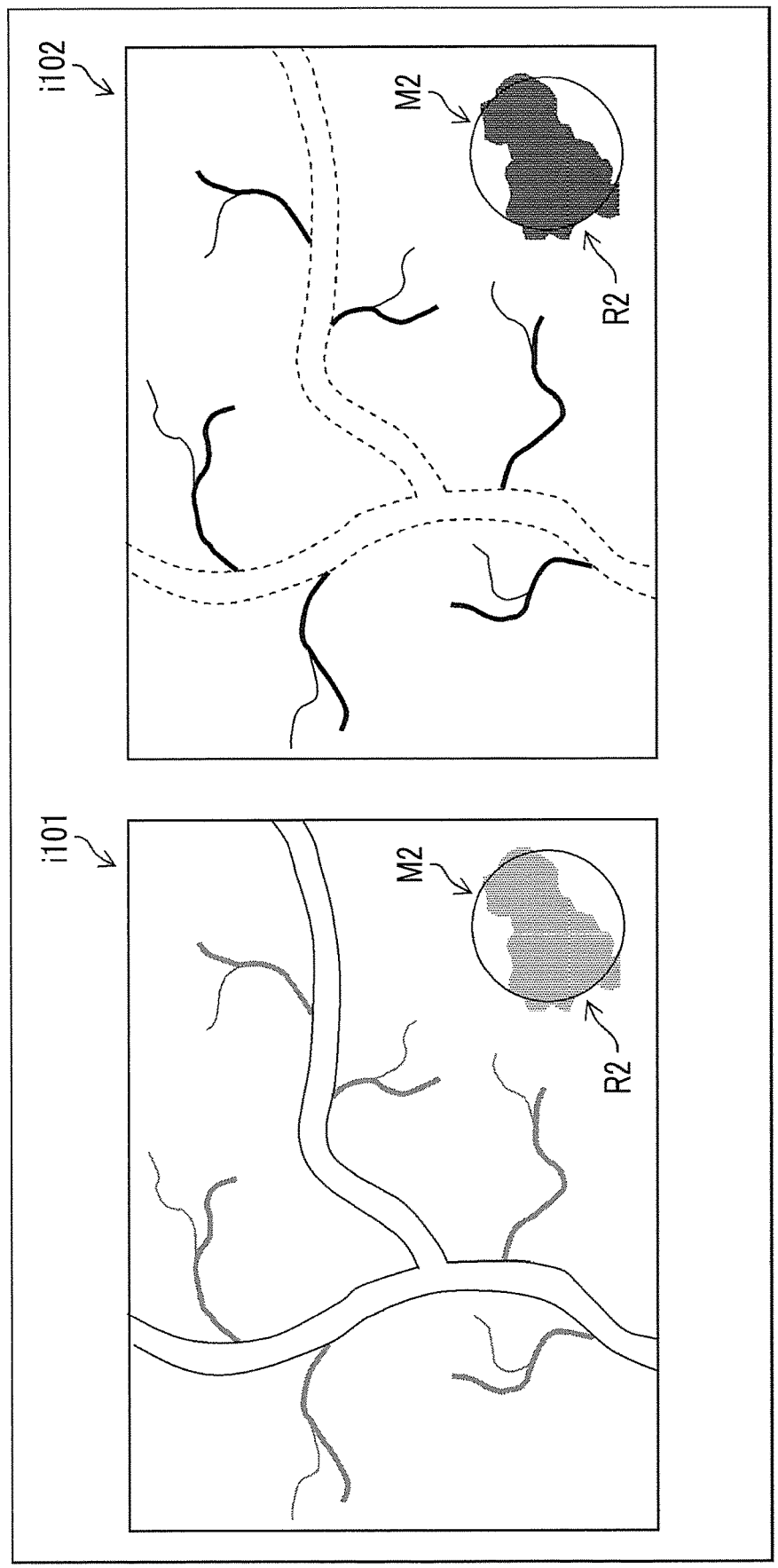
FIG. 12 is a diagram showing a state in which the first image and the second image are displayed.

In the first embodiment, the display control unit 204E, the detection result output unit 204I, and the classification result output unit 204J can output (display, store) the image for the second image, the detection result of the region of interest, and the classification result of the region of interest in addition to the output of the first image and/or the registered first image described above (display control step, first output step, second output step). With the output of the second image, the user can accurately detect and classify the region of interest or the like using the second image (blue narrow-band light in the above example) while continuously observing the first image using normal light (white light). FIG. 12 is a diagram showing a state in which an image i101 which is a first image (registered first image) and an image i102 which is a second image are displayed on the monitor 400, and a region of interest R2 is detected and a marker M2 for measuring a size thereof is displayed.

After outputting the registered first image, the image processing unit 204 determines whether to end processing or not (step S290). This determination can be made on the basis of a lapse of a preset time, an instruction input by the user via the operation part 208, or the like. In a case where the processing is to be continued (NO in step S290), the process returns to step S100 and the above-described processing is repeated.

As described above, in the endoscope system 10 according to the first embodiment, in a case where an image is acquired using a plurality of observation lights, it is possible to obtain an image in which a change in the tint and structure of a subject between frames is small while preventing a substantial decrease in a frame rate. This allows the user to observe the exact structure of the subject.

(Additional Remarks)

In addition to each aspect of the above-described embodiment, configurations to be described below are also included in the scope of the present invention.

(Additional Remark 1)

The medical image processing device comprising: the medical image analysis processing unit that detects a region of attention which is a region to be noticed on the basis of a feature quantity of pixels of a medical image; and the medical image analysis result acquisition unit that acquires an analysis result of the medical image analysis processing unit.

(Additional Remark 2)

The medical image processing device comprising: the medical image analysis processing unit that detects presence or absence of a target to be noticed on the basis of a feature quantity of pixels of a medical image, and the medical image analysis result acquisition unit that acquires an analysis result of the medical image analysis processing unit.

(Additional Remark 3)

The medical image processing device, in which the medical image analysis result acquisition unit acquires the analysis result of the medical image from a recording device, and the analysis result includes any one or both of the region of attention that is the region to be noticed included in the medical image and presence or absence of the target to be noticed.

(Additional Remark 4)

The medical image processing device, in which the medical image is a normal light image that is obtained through irradiation of light in a white range or light in a plurality of wavelength ranges as the light in the white range.

(Additional Remark 5)

The medical image processing device, in which the medical image is an image that is obtained through irradiation of light in a specific wavelength range, and the specific wavelength range is a range narrower than the white wavelength range.

(Additional Remark 6)

The medical image processing device, in which the specific wavelength range is a blue range or a green range of a visible range.

(Additional Remark 7)

The medical image processing device, in which the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

(Additional Remark 8)

The medical image processing device, in which the specific wavelength range is a red range of a visible range.

(Additional Remark 9)

The medical image processing device, in which the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

(Additional Remark 10)

The medical image processing device, in which the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

(Additional Remark 11)

The medical image processing device, in which the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

(Additional Remark 12)

The medical image processing device, in which the medical image is an in-vivo image that the inside of a living body is captured, and the in-vivo image has information of fluorescence emitted by fluorescent materials in the living body.

(Additional Remark 13)

The medical image processing device, in which the fluorescence is obtained by irradiating the inside of the living body with excitation light which has a peak in a range of 390 nm to 470 nm.

(Additional Remark 14)

The medical image processing device, in which the medical image is an in-vivo image that the inside of a living body is captured, and the specific wavelength range is an infrared wavelength range.

(Additional Remark 15)

The medical image processing device, in which the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

(Additional Remark 16)

The medical image processing device, in which the medical image acquisition unit comprises the special light image acquisition unit that acquires a special light image having information on a specific wavelength range on the basis of a normal light image obtained through irradiation of light in a white range or light in a plurality of wavelength ranges as the light in a white range, and the medical image is the special light image.

(Additional Remark 17)

The medical image processing device, in which a signal of the specific wavelength range is obtained by calculation based on color information of RGB or CMY included in the normal light image.

(Additional Remark 18)

The medical image processing device further comprising: a feature quantity image generation unit generating a feature quantity image by calculation based on at least one of the normal light image that is obtained through irradiation of light in a white range or light in a plurality of wavelength ranges as the light in the white range or the special light image that is obtained through irradiation of light in a specific wavelength range, in which the medical image is the feature quantity image.

(Additional Remark 19)

An endoscope device comprising: the medical image processing device according to any one of Additional remarks 1 to 18; and an endoscope that acquires an image obtained through irradiation of at least one of light in a white wavelength range or light in the specific wavelength range.

(Additional Remark 20)

The diagnosis support device comprising: the medical image processing device according to any one of Additional remarks 1 to 18.

(Additional Remark 21)

A medical service support device comprising: the medical image processing device according to any one of Additional remarks 1 to 18.

Although the embodiments and other aspects of the present invention have been described above, the present invention is not limited to the above-described aspects, and various modifications can be made without departing from the spirit of the present invention. For example, the present invention can be applied not only to a medical endoscope but also to an endoscope for diagnosing damage, deterioration, defects, and the like of industrial products such as mechanical parts. In addition, the present invention can also be applied to a case where a crack and a "float" are detected in structures such as a bridge, a road, a tunnel, or a building using a visible light image and an infrared image.

EXPLANATION OF REFERENCES

10: endoscope system
100: endoscope main body
102: hand operation part
104: insertion part
106: universal cable
108: light guide connector
112: flexible part
114: bendable part
116: distal end rigid part
116A: distal end rigid surface
123: illumination part
123A: illuminating lens
123B: illuminating lens
126: forceps port
130: imaging optical system
132: imaging lens
134: imaging element
136: drive circuit
138: AFE
170: light guide
200: processor
202: image input controller
204: image processing unit
204A: imaging control unit
204B: image input unit
204C: parameter calculation unit
204D: image generation unit
204E: display control unit
204F: image correction unit
204G: region of interest detection unit
204H: region of interest classification unit
204I: detection result output unit
204J: classification result output unit
205: image input interface
206: video output unit
207: storage unit
208: operation part
209: sound processing unit
209A: speaker
210: CPU
211: ROM
212: RAM
300: light source device
310: light source
310B: blue light source
310G: green light source
310R: red light source
330: stop
340: condensing lens
350: light source control unit
400: monitor
BT1: air supply and water supply button BT2: suction button
BT3: function button
BT4: imaging button
M1: arrow
M2: marker
R1: region of interest
R2: region of interest
S100 to S290: each step of image processing methods
V1: blood vessel
V2: blood vessel
i1: image
i2: image
i3: image
i4: image
i5: image
i5A: image
i6: image
i7: image
i8: image
i9: image
i10: image
i11: image
i12: image
i101: image
i102: image

What is claimed is:

1. An image processing device comprising:
a processor, configured to:
input a first image and a second image captured at different times, in which the first image is captured with first observation light and the second image is captured with second observation light different from the first observation light;
calculate a parameter by using the first image and the second image, wherein the parameter is a parameter for at least one of relative movement, rotation, or deformation between the first image and the second image;
apply the parameter to the first image to generate an intermediate image; and
cause a display device to sequentially display the input first image and the generated intermediate image.

2. The image processing device according to claim 1, wherein the processor calculates, as the parameter, a parameter for performing projective transformation between the first image and the second image, and
wherein the processor performs projective transformation based on the calculated parameter on the first image to generate the intermediate image.

3. The image processing device according to claim 1, wherein the processor acquires the first image captured at a capturing time which is before a capturing time of the second image and at which a time difference from the capturing time of the second image is equal to or less than a threshold value.

4. The image processing device according to claim 1, wherein the processor is further configured to:
perform correction on the first image and/or the second image to reduce a difference between the first image and the second image caused by a difference between the first observation light and the second observation light,
wherein the processor calculates the parameter for the corrected first image and the corrected second image.

5. The image processing device according to claim 4, wherein the processor extracts a component of a wavelength common to the first observation light and the second observation light from an image signal of the first image and an image signal of the second image, and
wherein the processor calculates the parameter on the basis of the extracted component.

6. The image processing device according to claim 5, wherein the processor weights at least one of the image signal of the first image or an image signal of the second image to make a signal intensity of a component having a wavelength common to the first observation light and the second observation light relatively stronger than a signal intensity of other components other than the component, and
wherein the processor calculates the parameter using the weighted image signal.

7. The image processing device according to claim 1, wherein the processor is further configured to:
detect a region of interest from the first image, the intermediate image, or the second image.

8. The image processing device according to claim 7, wherein the processor is further configured to:
output information indicating the region of interest.

9. The image processing device according to claim 8, wherein the processor superimposes the information indicating the region of interest on the first image and causes the display device to display the information.

10. The image processing device according to claim 7, wherein the processor is further configured to:
classify the region of interest on the basis of at least the second image out of the first image and the second image.

11. The image processing device according to claim 10, wherein the processor is further configured to:
output information indicating a result of the classification.

12. The image processing device according to claim 11, wherein the processor causes the display device to display the information indicating the result of the classification.

13. The image processing device according to claim 1, wherein the first observation light is white light including light in wavelength ranges of red, blue, and green, and the second observation light is narrow-band light corresponding to a wavelength range of any of red, blue, and green.

14. The image processing device according to claim 1, wherein the first observation light is first narrow-band light corresponding to a wavelength range of any of red, blue, and green, and the second observation light is a second narrow-band light corresponding to a wavelength range of any of red, blue, and green and having a wavelength range different from that of the first narrow-band light.

15. The image processing device according to claim 1, wherein the processor inputs, as the second image, an image captured using light having a center wavelength shorter than that of the first observation light as the second observation light.

16. An endoscope system comprising:
the image processing device according to claim 1;
the display device;
an endoscope that has an insertion part to be inserted into a subject, the insertion part having a distal end rigid part, a bendable part connected to a proximal end side of the distal end rigid part, and a flexible part connected to a proximal end side of the bendable part, and has an operation part connected to a proximal end side of the insertion part;

a light source device that irradiates the subject with the first observation light or the second observation light; and an imaging unit that has an imaging lens for forming an optical image of the subject and an imaging element on which the optical image is formed by the imaging lens, wherein the imaging lens is provided on the distal end rigid part.

17. An image processing method comprising:

inputting a first image and a second image captured at different times, in which the first image is captured with first observation light and the second image is captured with second observation light different from the first observation light are input;

calculating a parameter by using the first image the second image, wherein the parameter is a parameter for at least one of relative movement, rotation, or deformation between the first image and the second image;

applying the parameter to the first image to generate an intermediate image; and sequentially displaying the input first image and the generated intermediate image on a display device.

18. The image processing device according to claim 1, wherein the intermediate image is another first image at a capturing time of the second image, wherein the another first image is generated by applying a parameter of position alignment to the first image.

19. The image processing device according to claim 1, wherein the processor calculates the parameter on the basis of a component of a wavelength common to the first observation light and the second observation light from an image signal of the first image and an image signal of the second image.

20. The image processing device according to claim 1, wherein the processor further displays information indicating a region of interest detected from the first image, the intermediate first image, or the second image.

* * * * *